(12) United States Patent
Brinckerhoff et al.

(10) Patent No.: US 7,033,756 B1
(45) Date of Patent: Apr. 25, 2006

(54) METHODS OF DIAGNOSING, PROGNOSTICATING AND TREATING MATRIX METALLOPROTEINASE-1 RELATED DISEASES VIA A MATRIX METALLOPROTEINASE-1 SINGLE NUCLEOTIDE POLYMORPHISM

(75) Inventors: Constance E. Brinckerhoff, Norwich, VT (US); Joni L. Rutter, Silverspring, MD (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 09/856,749

(22) PCT Filed: Nov. 10, 1999

(86) PCT No.: PCT/US99/26610

§ 371 (c)(1),
(2), (4) Date: Aug. 12, 2002

(87) PCT Pub. No.: WO00/32819

PCT Pub. Date: Jun. 8, 2000

Related U.S. Application Data

(60) Provisional application No. 60/110,266, filed on Nov. 30, 1998.

(51) Int. Cl.
*C07H 21/04* (2006.01)
*C12Q 1/68* (2006.01)

(52) U.S. Cl. .......................... 435/6; 536/23.1
(58) Field of Classification Search ............ 435/6, 435/91.1, 91.2; 536/23.1, 24.3
See application file for complete search history.

(56) References Cited

U.S. PATENT DOCUMENTS

| | | | |
|---|---|---|---|
| 5,744,442 A | 4/1998 | Richards et al. ............... 514/2 |
| 5,856,094 A * | 1/1999 | Sidransky et al. ............. 435/6 |
| 5,989,885 A * | 11/1999 | Teng et al. ................. 435/194 |

OTHER PUBLICATIONS

Jurajda et al. (Molecular and Cellular probes, vol. 16, pp. 63-66, 2002).*
Lee et al. (Scand J. Rheumatol. vol. 32, pp. 235-239, 2003).*
Constantin et al. (J. of rheumatology, vol. 29, No. 1, pp. 15-20, Jan. 2002).*
Jurajda et al. Gynecol Obstet Invest. vol. 52, pp. 124-127, 2001.*
Zhang et al. (Stroke, vol. 32, pp. 2198-2202, 2001).*
Johnson et al. (Genes and Immunity, vol. 2, pp. 273, 2001).*
Louka et al. (Scand J. Gastroenterol. vol. 8, pp. 931-935, 2001).*
Matsumura et al. (J. Cancer Res. Clin. Oncol., vol. 130, pp. 259-265, 2004).*
Dermer et al. (Biotechnology vol. 12, Mar. 1994, p. 320).*
Aho et al. (Eur. J. Biochem. vol. 247, pp. 503-510, Jul. 1997).*
Przybylowska et al. (Experimental Oncology, vol. 24, pp. 25-27, Mar. 2002).*
Wenham et al. (J. of Soc. Gynecologic Investigation, vol. 10, No. 6, pp. 381-387, Sep. 2003).*
Lai et al. (Gynecologic Oncology, vol. 96, pp. 314-319, 2005).*
Ju et al. (Cancer letters, vol. 217, pp. 191-196, 2005).*
Babickova et al. (Studia Pneumologica et Phthiseologica, vol. 65, No. 3, pages abstract only, 2005).*
Wenham et al. (J. of the Society for Gynecologic Investigation, vol. 10, No. 6, pp. 381-387, 2003).*
Benbow et al. (J. of Cell. Biochemistry. vol. 86, pp. 307-319, 2002).*
Fang et al. (Carcinogenesis, vol. 26, No. 2, pp. 481-486, 2005).*
Logan et al., "synergistic Transcriptional Activation of the Tissue Inhibitor of Metalloproteinases-1 Promoter via Functional Interaction of AP-1 and Ets-1 Transcription Factors", *J. Biol. Chem.* 1996 271 (2):774-782.
Rutter et al., "A Single Nucleotide Polymorphism in the Matrix Metalloproteinase-1 Promoter Creates an Ets Binding Site and Augments Transcription[1]", *Cancer Research* 1998 58:5321-5325.
Westermarck et al., "Differential regulation of interstitial collagenase (MMP-1) gene expression by ETS transcription factors", *Oncogene* 1997 14:2651-2660.
White et al., "ETS Sites in the Promoters of the Matrix Metalloproteinases Collagenase (MMP-1) Stromelysin (MMP-3) are Auxiliary Elements that Regulate Basal and Phorbol-Induced Transcription", *Connective Tissue Research* 1997 36(4):321-335.

* cited by examiner

*Primary Examiner*—Jeanine A. Goldberg
(74) *Attorney, Agent, or Firm*—Licata & Tyrrell P.C.

(57) ABSTRACT

Methods and kits for diagnosing and prognosticating matrix metalloproteinase-1 related disease by detecting a single nucleotide polymorphism in the promoter of the gene are provided. Also provided are methods of identifying agents which inhibit binding of transcriptions factors to the Ets transcription factor binding site created by or resulting from this single nucleotide polymorphism and methods of using these agents to treat matrix metalloproteinase-1 related diseases.

1 Claim, No Drawings

METHODS OF DIAGNOSING, PROGNOSTICATING AND TREATING MATRIX METALLOPROTEINASE-1 RELATED DISEASES VIA A MATRIX METALLOPROTEINASE-1 SINGLE NUCLEOTIDE POLYMORPHISM

This application claims benefit of priority under 35 U.S.C. §371 to PCT application No. PCT/US99/26610, filed Nov. 10, 1999, which claims benefit under 35 U.S.C. §119 to U.S. Provisional Patent Application Ser. No. 60/110,266, filed on Nov. 30, 1998.

This invention was made in the course of research sponsored by the National Institutes of Health. The U.S. Government may have certain rights in this invention.

BACKGROUND OF THE INVENTION

Matrix metalloproteinases (MMPs) are a family of at least 15 enzymes that degrade the extracellular matrix (ECM) (Borden, P. and Heller, R. Crit. Rev. Eukaryotic Gene Expr. 7: 159–178, 1997). These enzymes have essential roles in modeling and remodeling the ECM in normal physiology and disease pathology. Several of these enzymes have the unique ability to degrade the interstitial collagenase (types I, II, and III), the body's most abundant proteins. MMP-1 is the most ubiquitously expressed interstitial collagenase, thereby assigning it a prominent role in collagen degradation. Overexpression of MMP-1 is associated with several pathological conditions, including the irreversible degradation of cartilage, tendon, and bone in arthritis (Vincenti et al. Crit. Rev. Eukaryotic Gene Expr. 6:391–411, 1996) and the degradation of collagenase I and III in tumor invasion and metastasis (Chambers, A. F. and Matrisian, L. M. J. Nat'l Cancer Inst. 89:1260–1270, 1997; Murray et al. Nat. Med. 2:461–462, 1996). Patients with tumors that express MMP-1 have an overall poorer prognosis than patients with tumors that do not express this protein (Murray et al. Nat. Med. 2:461–462, 1996; Murray et al. J. Pathol. 185:256–261, 1998). This overexpression of MMP-1 has been suggested to be due to the juxtaposition of transcription factor binding sites within the promoter of this gene and to the cooperativity among the factors that bind these sites (Buttice et al. Oncogene 13:2297–2306, 1996; Basuyaux et al. J. Biol. Chem. 272:26188–26195, 1997; Gutman, A. and Waslyk, B. EMBO J. 9:2241–2246, 1990; Benbow, U. and Brinckerhoff, C. E. Matrix Biol. 15:519–526, 1997).

Most normal cells express modest, but detectable, levels of MMP-1 constitutively, and this expression increases substantially in the presence of cytokines or growth factors (Vincenti et al. Crit. Rev. Eukaryotic Gene Expr. 6:391–411, 1996; Rutter et al. J. Cell Biochem. 66:322–336, 1997; Aho et al. Eur. J. Biochem. 247:503–510, 1997; Delany, A. M. and Brinckerhoff, C. E. J. Cell Biochem. 50:400–410, 1992). However, A2058 melanoma cells constitutively express high levels of MMP-1 (Templeton et al. Cancer Res. 50:5431–5437, 1990), making them a useful model for studies on the transcriptional regulating of this gene and for comparative studies with normal cells.

A 4 kb region of the MMP-1 promoter DNA from a leukocyte genomic library was isolated and sequenced (Rutter et al. J. Cell Biochem. 66:322–336, 1997). DNA sequence analysis revealed that this clone contained only 1 G at position –1607 bp, resulting in the sequence 5'-AAGAT-3' (SEQ ID NO: 1) (Rutter et al. J. Cell Biochem. 66:322–336, 1997). This sequence differs from that reported by others (Aho et al. Eur. J. Biochem. 247:503–510, 1997; Imai et al. Mol. Cell Biol. 14:7182–7194, 1994), wherein 2 Gs at that location which create the sequence 5'-AAGGAT-3' (SEQ ID NO: 2) are described. The presence of 2 Gs at this site creates the sequence 5'-GGA-3', which is a consensus sequence (Graves, J. B. Science 279:1000–1001, 1998) for a functional PEA3/EBS. This site has now been established to constitute a single nucleotide polymorphism (SNP). The full length DNA sequence of MMP-1 with only 1 G at position –1607 is depicted in SEQ ID NO: 3.

Based upon the effect of this SNP on the transcriptional activity, protein/DNA binding activity, and frequency of this SNP in normal fibroblasts and in melanoma tumor cells it has now been determined that detection of this SNP is useful in diagnosing and prognosticating cancer and other MMP-1 related diseases. It is also now believed that agents identified as inhibitors of binding of transcription factors to the Ets transcription factor binding site created by or resulting from this SNP will be useful in treating MMP-1 related diseases.

SUMMARY OF THE INVENTION

An object of the present invention is to provide a method of diagnosing MMP-1 related diseases in a patient which comprises detecting in a patient MMP-1 containing an Ets transcription factor binding site single nucleotide polymorphism (MMP-1 EBS-SNP).

Another object of the present invention is to provide a method of prognosticating MMP-1 related diseases in a patient which comprises detecting in a patient suffering from an MMP-1 related disease an MMP-1 EBS-SNP.

Another object of the present invention is to provide a kit for diagnosis and prognosis of an MMP-1 related disease in a patient via detection of MMP-1 EBS-SNP in a patient sample.

Another object of the present invention is to provide a method of identifying agents with potential therapeutic value in treating MMP-1 related diseases which comprises screening agents for the ability to inhibit the binding of a transcription factor to an MMP-1 EBS-SNP.

Yet another object of the present invention is to provide a method of treating MMP-1 related diseases in a patient which comprises administering to the patient an agent which inhibits binding of a transcription factor to an MMP-1 EBS-SNP.

DETAILED DESCRIPTION OF THE INVENTION

The abundance of single nucleotide polymorphisms (SNPs) in the genome make these genomic variations powerful tools for identifying disease genes, particularly in loss of heterozygosity studies in tumors. A large effort is presently underway for identifying SNPs. Most research is focused on the coding regions of genes (Wang et al. Science 280:1077–1082, 1998).

However, an SNP located in the promoter of the interstitial collagen degrading enzyme, MMP-1, has now been identified. Because this variation is not located in a coding region, it does not alter the structure of the enzyme. However, the location of this SNP in the promoter region of MMP-1 has now been demonstrated to have profound effects on the production/regulation of the enzyme. Further, an increase in the frequency of this SNP in tumor cell lines has now been demonstrated which is indicative of this SNP causing an increase in invasive behavior due to high levels of MMP-1 expression. MMP-1 is implicated in tumor cell invasion and metastasis due to its ability to cleave the interstitial collagenase types I and III at neutral pH. Therefore, a structural variation with the potential to influence the level of expression is important to understanding how this enzyme modulates ECM metabolism and tumor cell invasion and metastasis. Further, detection of this SNP in a patient is useful in diagnosing and prognosticating MMP-1 related diseases.

The effects of this SNP, referred to herein as MMP-1 EBS-SNP, on the transcriptional activity and protein/DNA binding activity, along with the frequency of this SNP in normal fibroblasts and in melanoma tumor cells were examined in detail.

Constitutive mRNA expression of endogenous MMP-1 gene in normal foreskin fibroblasts (HFS) and in the A2058 melanoma cells over a 24 hour period was determined. HFS expressed low levels of MMP-1 mRNA, while A2058 cells expressed higher levels. To determine whether the A2058 cells contained a difference in the endogenous MMP-1 promoter, polymerase chain reaction (PCR) was used to amplify the promoter from these cells. This sequence was then compared with the previously isolated leukocyte clone described by Rutter et al. J. Cell Biochem. 66:322–336, 1997 and set forth in SEQ ID NO: 3 and with promoters from other sources (Aho et al. Eur. J. Biochem. 247: 503–510, 1997; Imai et al. Mol. Cell Biol. 14:7182–7194, 1994). Several substitutions were observed, but were considered insignificant because they did not create or delete any known binding sites for transcription factors within the promoter. However, one major difference was detected: the A2058 promoter DNA contained an additional G at position −1607 bp, which was flanked by a guanidine (5') and an adenine (3'), thus creating an Ets transcription factor binding site (EBS; Graves, B. Science 279:1000–1001, 1998).

To specifically test the role of the 1 G/2 G variation in regulating transcription, two luciferase reporter constructs driven by a large (4.3 kb) fragment of the MMP-1 promoter were generated with the only difference being 1 G or 2 Gs at −1607 bp. This SNP is adjacent to an AP-1 site −1602 bp, which may also influence transcription. These clones were transitely transfected in HFS and the effect on basal transcription was measured. A significant increase (ranging from 2–10-fold) in transcription with the 2 G promoter construct compared with the 1 G promoter construct was consistently observed in at least four separate donors of HFS. Hirt's analysis of transfected DNA demonstrated that the differences were not attributable to transfection efficiency. When these two constructs were transfected into the A2058 melanoma cells, a 29-fold increase in transcription of the 2 G construct over the 1 G construct was observed. Other experiments showed similar increases ranging from 1- to 37-fold. These constructs were then tested in other tumor cell lines (MDA231 breast cancer cells, and two primary melanoma lines) to assess their transcriptional response. In these cells, the 2 G promoter construct augmented transcription at least 4-fold over the 1 G construct. Thus, the increase in transcription is dependent on the presence of 2 Gs at −1607 bp, and it is seen in both normal and malignant cells.

The ability of an oligo probe containing either 1 G or 2 Gs at −1607 bp to bind to nuclear extracts from the A2058 cells was also assessed. A striking difference in binding intensity was seen, with the 2 G oligo binding more nuclear proteins compared with the 1 G oligo. Thus, the presence of the 2 Gs clearly augments this binding. Cross competition experiments were used to determine the specificity of binding to each labeled oligo. Binding to the 1 G oligo was readily competed, suggesting that these DNA/protein interactions are weak. Competition studies with the 2 G oligo revealed that the "self" oligo only mildly competed the binding of the shared bands, although it did compete two bands, demonstrating that these proteins bind preferentially and/or specifically to the 2 G oligo. Furthermore, the 1 G oligo did not compete well, but was effective in competing the shared bands. Finally, the proximal EBS-AP-1 competitor showed a pattern similar to that seen with the 1 G oligo. Taken together, these observations indicate that the 2 G "self" oligo competes for the proteins able to bind specifically to the 2 gene sequence, and that the other bands represent proteins or protein complexes that are not 2 G-dependent (e.g. the AP-1 proteins). Importantly, these data also indicate that the presence of the EBS in this region of MMP-1 creates an environment where DNA/protein interactions strongly occur.

Because the SNP at −1607 bp is located adjacent to an AP-1 site at −1602 bp, binding to the 1 G and 2 G oligos by recombinant ETS-1 and c-JUN, proteins that are likely candidates for binding to these sites, was investigated. The recombinant proteins, by themselves, were not able to bind to either oligo. The combination of both proteins, however, bound to the 2 G oligo, but only faintly to the 1 G oligo, suggesting that additional proteins were required for optimal DNA binding. Indeed, incubation with nuclear extract from A2058 cells resulted in distinctive binding patterns for each probe. Complexes I, II, VI, and VII were present in both panels, whereas complexes III, IV, and V were specific for the 2 G oligo. When ETS-1 and c-JUN were added together with nuclear extract, binding to the 2 G oligo was more pronounced compared with the 1 G oligo.

In the presence of recombinant c-JUN, complex I became more apparent with both oligos, indicating that complex I may represent AP-1 proteins binding to the DNA. Complex VII also became more intense when c-JUN was added indicating that it, too, contains AP-1 related proteins. When both recombinant proteins were added, the binding pattern in the 1 G panel did not differ from the reactions with c-JUN alone, supporting the importance of 2 Gs in creating the EBS. When nuclear extracts and recombinant ETS-1 were added to the 2 G oligo, a new complex was formed (complex IV). Furthermore, when both proteins and nuclear extract were added to the 2 G probe, several complexes (I, III, IV, V, and VI) were diminished and seemed to combine into a much stronger complex II, again demonstrating the influence of the 2 Gs in creating EBS.

Antibodies to several members of the Ets family of transcription factors (ETS-1/2, Erg-1/2, Elk-1 and ERM) were used in "super/shift" reactions to identify the proteins binding to this site. However, binding of these antibodies was not detected due either to limitations of the antibodies, because the complexes did not allow for the antibody to have access to the epitope, and/or because these proteins did not bind. These data suggest that the oligos containing 2 Gs represents a bona fide EBS that binds an Ets family member(s) in a complex with AP-1 protein members. While the data show that recombinant ETS-1 binds, it is believed that other Ets family members can also bind to this site.

Confirmation of this 1 G/2 G difference in the leukocyte clone sequence and the A2058 melanoma sequence, to be a SNP and not a mutation, was performed. A radiolabeled PCR assay using primers that flank the variation to amplify a product of either 148 bp (1 G), 149 bp (2 G), or both (heterozygous) in genomic DNA was developed. One hundred control DNAs derived from the CEPH pedigrees (cephb with the extension .fr/cephdb/ of the world-wide web) were then assayed to determine the frequency of this variation within a population. Only the parents in the pedigrees were used to avoid biasing the results through inheritance. In addition to the CEPH control DNAs, the frequency of this SNP in several tumor cell lines, including the A2058 melanoma cells, was assessed. The occurrence of 2 G homozygotes in the CEPH controls was determined to be approximately 30%. In the tumor cells lines, it is 62.5% ($P<0.0001$).

Accordingly, based upon these experiments, it is believed that the 1 G/2 G SNP influences the transcriptional responsiveness of the human MMP-1 promoter in cancer, where excessive production of MMP-1 is a major contributor to the stromal degradation involved in tumor invasion. As with other genes, expression of MMP-1 is meditated by multiprotein complexes that bind to DNA in a sequence-specific manner, and these complexes often cooperate to achieve maximal activation. DNA elements containing a single EBS are often not sufficient for Ets induction, and require a nearby AP-1 site to which Fos and JUN proteins bind. Furthermore, the transcriptional environment within the cells may influence the level of gene expression, as evidenced by differences in the level of transcription of the 2 G allele in HFS versus melanoma cells. These differences may be due to various extracellular stimuli, such as growth factors and cytokines, as well as cell-type-specific nuclear factors within the cell. Thus, the combination of cis-acting sequences in the MMP-1 promoter and specific trans-acting factors can dramatically increase transcription. This increase is believed to provide a molecular mechanism for enhanced ECM degradation not only in cancer, but in other MMP-1 related diseases such as arthritis, cardiovascular disease and periodontitis.

For example, rheumatoid arthritis, a chronic disease that afflicts more than two million individuals in the United Stated and 1% of the population world-wide is characterized by severe and irreversible degradation of cartilage, tendon and bone mediated by overexpression of MMPs. Inflammatory cytokines such as interleukin-1 and tumor necrosis factor-α activate synovial fibroblasts that line the joint and adjacent chondrocytes to produce these MMPs. Destruction of interstitial collagen occurs mainly through two MMP family members, MMP-1 and MMP-13. MMP-1 and MMP-13 are expressed by synovial fibroblasts and articular chondrocytes. It is believed that, in similar fashion to patients suffering from cancer, overexpression of MMP-1 in patients suffering from rheumatoid arthritis may result at least in part from this SNP.

Accordingly, detection of the MMP-1 EBS-SNP in a patient provides a useful means for diagnosing MMP-1 related diseases. Detection of MMP-1 EBS-SNP in a patient is indicative of the patient suffering from a disease relating to overexpression of the MMP-1 enzyme. Detection of this SNP can be performed in accordance with well known techniques including, but not limited to, PCR as described herein.

Detection of MMP-1 EBS-SNP also provides a useful method for prognosticating MMP-1 related diseases in a patient. For example, it is well known that MMPs are key players in tumor invasion and metastasis. Both processes require degradation of the extracellular matrix, which is accomplished by proteolytic enzymes that are secreted by either tumor cells, themselves, and/or neighboring stromal cells. In fact, at least for melanoma cells which produce MMP-1, the prognosis of the disease is correlated with tumor thickness and depth of invasion through dermal collagens (I and II), thereby indicating that invasiveness through these collagens serves as a valid prognostic marker. Accordingly, detection of MMP-1 EBS-SNP, which is indicative of enhanced ability to degrade collagen types I, II and III, in tumor cells of a patient serves as a useful prognostic marker in assessing the invasiveness of a particular tumor. This prognostic marker is thus useful in determining various treatment regimes expected to be most successful in individual patients.

Means for detecting MMP-1 EBS-SNP in a patient sample for diagnosing and/or prognosticating MMP-1 related diseases can be incorporated into a kit for easy use by a laboratory technician. In one embodiment, the kit can comprise PCR primers such as those described in Example 5 herein which flank the MMP-1 EBS SNP. In this embodiment, the kit may also comprise dGTP, dATP, dTTP, and dCTP; Taq DNA polymerase; and α(32)P-dCTP. However, other means for detecting the MMP-1 EBS-SNP which can be incorporated into a kit will be obvious to those of skill in the art upon this disclsoure. Kits of the present invention may also comprise positive and negative control samples.

Further, inhibiting MMP-1 synthesis by targeting either the MMP-1 EBS-SNP or proteins that bind to this SNP represents a useful therapeutic approach to inhibit pathologic expression of MMP-1, but not its normal physiological role. Potential therapeutic agents for treatment of MMP-1 related diseases including, but not limited to, cancer, rheumatoid arthritis, cardiovascular disease and periodontitis, can be identified by determining their ability to either bind to MMP-1 EBS-SNP, to bind to proteins which bind to MMP-1 EBS-SNP or to inhibit binding of MMP-1 EBS-SNP with other proteins. Agents identified by this method can then be administered to patients suffering from an MMP-1 related disease to alleviate the symptoms resulting from overexpression of MMP-1.

The following nonlimiting examples are provided to further illustrate the present invention.

EXAMPLES

Example 1

Cells and Plasmids

Primary human foreskin fibroblasts (HFF) were prepared in accordance with procedures described by Rutter et al. J. Cell Biochem. 66:322–336, 1997, and used during passages 4–8. HFFs and A2058 cells were cultured in DMEM (Life technologies, Inc.) with 10% fetal bovine serum (Sigma Chemical Co.), penicillin (100 units/ml), and streptomycin (100 µg/ml).

A 4.3-kb MMP-1 promoter DNA fragment containing only 1G at −1607 bp was described by Rutter et al. J. Cell Biochem. 66:322–336, 1997. Primers were made to amplify the endogenous promoter from the A2058 cells (−4008 bp to −3988 bp sense primer: 5'-GTGGAAGCTTACAC-CTATAATCCCAACACTC-3' (SEQ ID NO: 4) and −511 bp to −543 bp antisense primer: 5'-CTGCCTGGTACCCTAT-TGCGATAGCACCATGGC-3' (SEQ ID NO: 5). Two A2058 PCR amplified clones were subcloned into the pBL5CAT (Promega) vector and sequenced to ensure the absence of PCR artifacts. Reporter clones were then constructed in which the only difference between the two pGL3-MMP-1 vectors was the SNP at position −1607 bp. First, the MMP-1 promoter insert from the pXP2 vector was subcloned into the pGL3 Basic vector (Promega). Unique sequences flanking the G variation were restricted by AatII (5') and EcoRV (3'), thereby isolating a 450/451-bp fragment from the leukocyte clone in pGL3 Basic (1 G) and A2058 melanoma DNA in pBL5CAT (2 Gs), respectively, and excluding any other sequence variations found in the A2058 promoter. Finally, the 451-bp insert containing the 2 Gs was "swapped" and ligated into the pGL3-MMP-1 construct containing AatII/EcoRV ends, thereby generating the two SNP constructs.

Example 2

Northern Analysis

Confluent cultures in 150-mm diameter tissue culture dishes were washed and placed in 10 ml of serum-free DMEM plus 0.2% lactalbumin hydrolysate. Immediately (time 0) and at 24 hours, total RNA was isolated using the TRIzol reagent (Life Technologies, Inc.) and 20 µg were subjected to Northern analysis and hybridized with cDNA-specific probes for MMP-1 or glyceraldehyde-3-phosphate dehydrogenase. Probes were random prime labeled with $\alpha((32)P$-dCTP (12.5 µCi/reaction of 3,000 Ci/mmol) and hybridized for 20 hours at 56° C.

Example 3

Transfection and Luciferase Assay

Transient transfections were performed in triplicate in accordance with procedures described by Rutter et al. J. Cell Biochem. 66:322–336, 1997 with the LipofectAMINE PLUS reagent (Life Technologies, Inc.) using 2 µg of the chimeric MMP-1 promoter/reporter plasmids, 5 µl of the PLUS reagent, and 5 µl of LipofectAMINE. Luciferase activity is reported as RLUs. Hirt's analyses were performed and normalized to RLUs to control for any variations in transfection efficiency. Statistics were performed using the InStat Program (GraphPad Software) using the Welch's alternate t test, a modification of the unpaired t test.

Example 4

Nuclear Extract Preparation and EMSAs

Extracts of nuclear proteins were prepared, and EMSAs were performed as described by Schroen, D. L. and Brinckerhoff, C. E. J. Cell Physiol. 169:320–332, 1996, with $1 \times 10^5$ cpm of $\gamma^{32}P$-ATP end-labeled oligo incubated with nuclear extract (5 µg) and/or recombinants ETS-1 protein (2 µM) and c-JUN protein (1 µg; Promega). The samples were subjected to 5% PAGE at 150 V, dried, and autoradiographed. Oligos used for EMSAs were 1G sense, 5'-AAATAATTAGAAAGATATGACTTATCT-CAAATCAA-3' (SEQ ID NO: 6); 2 G sense, 5'-AAATAATTAGAAAGGATATGACTTATCT-CAAATCAA: (SEQ ID NO: 7) –88/–73 sense, 5'-TTCAT-TGTTAATCAAGAGGATGTTATAAAGCAT-GAGTCACACCCTCAGCTT-3' (SEQ ID NO: 8). The –88/–73 oligo spans the region –110 to –61 bp and includes the locations within the oligo that correspond to the proximal PEA3/AP-1 sites at the –88/–73, respectively.

Example 5

Radiolabeled PCR Assay

Primers that flank the SNP in MMP-1 were used for PCR amplification (sense primer, 5'-GTTATGCCACTTAGAT-GAGG-3' (SEQ ID NO: 9); antisense primer 5'-TTCCTC-CCCTTATGGATTCC-3' (SEQ ID NO: 10)). A typical reaction consisted of ~20 ng of DNA template; 0.2 mM dGTP, dATP, and dTTP, 2.5 µM dCTP; 10× buffer and Taq DNA polymerase (Sigma Chemical Co.); and $\alpha(32)P$-dCTP (Du-Pont/NEN). Reactions were PCR amplified (MJ Research PTC100 THERMOCYCLER) in 25 cycles (4 minutes at 94° C.; 45 seconds at 94° C., 45 seconds at 58° C., and 45 seconds at 72° C.; followed by a brief extension (10 minutes) at 72° C.). Following amplification, the reactions (2.5 µl) were mixed with 10× loading buffer and denatured for 2 minutes at 80° C. Samples were loaded onto an 8% denaturing PAGE and electrophoresed for 3 hours. Gels were dried and autoradiographed for approximately 15 minutes. Control samples generated from the plasmid clones were loaded on each gel for accurate scoring of the alleles. Statistics were calculated using the InStat Program (GraphPad Software) and were based on the percentage of the total number tested.

What is claimed is:

1. A method for detecting overexpression of matrix metalloproteinase-1 in a cell comprising detecting in the matrix metalloproteinase-1 promoter sequence a 5'-AAGAT-3' to 5'-AAGGAT-3' Ets transcription factor binding site single nucleotide polymorphism, wherein the promoter comprises SEQ ID NO:6, wherein the presence of the polymorphism is indicative of matrix metalloproteinase-1 overexpression in the cell.

* * * * *

UNITED STATES PATENT AND TRADEMARK OFFICE
CERTIFICATE OF CORRECTION

| | | |
|---|---|---|
| PATENT NO. | : 7,033,756 B1 | Page 1 of 1 |
| APPLICATION NO. | : 09/856749 | |
| DATED | : April 25, 2006 | |
| INVENTOR(S) | : Brinckerhoff et al. | |

It is certified that error appears in the above-identified patent and that said Letters Patent is hereby corrected as shown below:

Title Page;

(75): Please delete "Silverspring, MD (US)" and insert --Silver Spring, MD (US)--.

Signed and Sealed this

Eighteenth Day of December, 2007

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 5
<212> TYPE: DNA
<213> ORGANISM: Homo sapiens

<400> SEQUENCE: 1 aagat                                                                    5

<210> SEQ ID NO 2
<211> LENGTH: 6
<212> TYPE: DNA
<213> ORGANISM: Homo sapiens

<400> SEQUENCE: 2 aaggat                                                                   6

<210> SEQ ID NO 3
<211> LENGTH: 4438
```

```
<212> TYPE: DNA
<213> ORGANISM: Homo sapiens

<400> SEQUENCE: 3
cctcacatat ttcaaatcca tctcaaattc acattcacag atgtaagagc tgggaaagga      60
cggttttgac agggctgaac tgagctatgg tatgagtagc actcatcccc agaaagtctc     120
ttggtttgaa tttccgggaa aaggagctat agctgcaaaa atctgtttca caaatgtgct     180
aactataagc attttccaca gtgtttaata aaccatgcag ataagaaaat attattgaca     240
aacaaattaa taaaatgctc aaaataatct gatactaaat gcttgtagca tggcatgcaa     300
atcaccaaaa ataaatgtgc tatgcttcat ataaaatctc cagtaaggct gggtgtggtg     360
gctcacacct ataatcccaa cactctggga ggccgaggtg agagaactgc ttgaggccag     420
gagtttgaga ctagcctggc caacatagtg agacctcatc tctacaaaaa atcttaaaaa     480
tcagtgggac atggtggtgc acatctgtag ttctagctac ttgggagtct gaggcaggaa     540
gattgcttaa gcccaagagt ttgaggtccc tacactccag cctaagcgac agagggagac     600
cttgtctcta aataaataaa ttagttaatt gaatgtccag tcagttgata tatccaaatt     660
cttcccatgg taattttaaa aactttagtc ttaggagagt aaaagtcatg gacataagac     720
ttcttataaa caactcagcc taatgagaaa tagaccctgt atttaagtgt catttaagta     780
tctatttctt cattgatcta ttcatttatt aactcctgta acaatcattt gcagacacct     840
actatgttga ggtagtataa actataaatt caacaagttt gataagggaa ataagagaga     900
ttgagtgaca gcttgaaggg gaggattctt tcaggcctgt gggaccgggt ggtggcatgg     960
agacattatt gtggacttga gggagttaat gtgacagtcc tcgtgtctcc agacactttc    1020
tctctgttag ggaagcaaga tttctatccc cagagtatgt atgtgttatg tctggactgc    1080
agtggcacag aactgtgttc aacgagtgac taccgctctg ctgtgtgccc tgggacttgg    1140
ggttaattga tcaatcattt ctatccagaa ggtaaccatg aggactgacg gaaccagtgt    1200
gtaccaagtg tctgttaagt gtctggtcaa tggttatcca taaagctact gcatggccat    1260
atgtaggaag aatacacacc gtgagcaaat ttttcccacg tgtaactctc acaacaaaat    1320
agcattaaat acttaatgtt tctggctaaa gaccatttca agcttgcag acaaaaaaa    1380 tagaaaaaat atctgacact caaatggagt tacaaaatta aaacggctga attccccagc    1440
ataaaaaaat atgaagcaag attgaaattt caagactaag tttaatatgg aaaaatacaa    1500
atatgtttga ggcctttcac agagcagcca gcatgaagca accaagaaaa ccacggaaat    1560
aatctggctg cctggaaata gtccggagtc agctgacaca gccacacgag agccctctta    1620
tgcttgtcat aagggtaaa ggaataattt cagaaaatta catttaaaag agaattatgg    1680
gggaagaaga tgctcccaga ggaaacaaat agtatggatg tgaagagcaa atacaacttt    1740
aacatgtttt gaacttcttg gaaactatgc taagtttagg cattgctagg atttggtatg    1800
atttaatccc cagctttctg ttctaaattt ttgttttctt ttttactctc aaataaatca    1860
tatgctagca ccagctgcaa agttacatat gttgtattag acgatcttcc atgaatacct    1920
aactggaaat tccaagattc agggccatgt gaatctaggc tggctgctta accaaaactt    1980
aatttaattt ttttcgttta ttttaggaaa aaaaattaac gaaaagatgt ttcaagcaac    2040
cagtttccaa tccacgtcag caactatgac atttaatgaa acactgtgag catttagcat    2100
gagagctctg gactcagatg cagggagctt tgctagagaa gggaggaaaa agcaggcatg    2160
atgtggcggg ttgtgggga ctccaaggct ctatttccaa cttccatcag agaacttctg    2220
```

-continued

```
ttttcacctg gttttcaaat ttgctttcca aagggatttt tgtttaagta aaggatacag      2280
aggtttataa aagtttgaaa acttctacat tgcaggatgt gcaggctctt gccagatggg      2340
acagtgtatg agactcttcc agggtgacgt cttaggcaat ttcctgtcca atcacagatg      2400
gtcacatgct gctttcctga gttaacctat taactcaccc ttgtttccca ggcctcagtg      2460
gagctaggct tgtcacgtct tcacagtgac tagattccct cacagtcgag tatatctgcc      2520
actccttgac tttaaaaaca tagtctatgt tcaccctcta atatgaagag ccccttttcac     2580 tattttcttt gtctgtgctg gagtcacttc agtggcaagt gttctttggt ctctgccgca      2640
ccctccctct gatgcctctg agaagaggat ttccttttcg tgagaatgtc ttcccattct      2700
tcttaccctc ttgaactcac atgttatgcc acttagatga ggaaattgta gttaaataat      2760
tagaaagata tgacttatct caaatcaatc caagatatac tgaagtattg tttatgagta      2820
agatatcagt cttgacgcag aaagaaaaca ggaatccata aggggaggaa agtgttgaaa      2880
agcaaacctg atacagtggg aaaggtggga gacaccataa ggtgctgaag tgataaaaca      2940
ggccagtgtt tctccactgt atgttttcaa taaatgcttc caaggaagga gagtggggca     3000
tgagtagggg agctacagag ataaaccaac ttttcttacc aggaatgcta cagatagcac      3060
tggtgacacc ggtcaccagt acccaagaca atttaatgtg gaacataagt acaggaatac      3120
acatctttca ttacagagcc atgtatttat tttaatgggc aggagatgct aaataagatc      3180
ttttgaatgg aggaatgcat aaatatatga atgaatgcat acatgaaaga ataaataaat      3240
gctgcctagc accaaggagc gaagatagac tcatatcaag ggaaacaagt atgattaaaa      3300
ataagacccc agagtcacgc tcagtctctt tccagccttt tcatcatccg gtacattcag      3360
acaagtttca gggaaggatc ctatttgtcc catgataatg atgggcaagg ggtggggagt      3420 tatctctatac tccgcctgtg gatgagggg cttctcaggt aaggctctta aatcctaggc      3480
ctgagtaaat ttttttcaaat tttattttag acagggtccc tctctgttgc ctaggctgga      3540
gtgcagcggc acaatcacag ctcaatgcag cctcaacctc ccaggcccaa gtgatcctcc      3600
cacctcagcc tcttcagtga ctaggactac aggtgcatga ctccatgctt ggctaacttt      3660
aaaaaatgtt tgtttgtttg tttgtttttt acagagatgg ggtctcacca tgttgcccag      3720
gctgatcttg aactcctggg ctcaagtgat tccctgcct cggcctcctg aaattctggg       3780
attataggct tgagccacca tgcctggctc tgagtaaaga ttaagggaag ccatggtgct      3840
atcgcaatag ggtaccaggc agcttaacaa aggcagaagg gaacctcaga gaaccccgaa      3900
gagccaccgt aaagtgagtg ctgggggagc tgaacttcag tcagtacagg agccgaacag      3960
ccatcaggtg cgcagtgtta gtaattccac cctctgccct gggagcaagg tgtgtggaga      4020
aacctgtagc actttatgac catcagaacc agccttttc aaaaagacca tggagtactc       4080
tttgacctgt gtatataaca agaacctttc tcaaatagga aagaaatgaa ttggagaaaa      4140
ccactgttta catggcagag tgtgtctcct tcgcacacat cttgtttgaa gttaatcatg      4200
acattgcaac accaagtgat tccaaataat ctgctaggag tcaccatttc taatgattgc      4260
ctagtctatt catagctaat caagaggatg ttataaagca tgagtcagac acctctggct      4320
ttctggaagg gcaaggactc tatatataca gaggagcttt cctagctggg atattggagc      4380
agcaagaggc tgggaagcca tcacttacct tgcactgaga aagaagacaa aggccagt        4438
```

<210> SEQ ID NO 4
<211> LENGTH: 31
<212> TYPE: DNA
<213> ORGANISM: Artificial Sequence

```
<220> FEATURE:
<223> OTHER INFORMATION: Description of Artificial Sequence:Synthetic

<400> SEQUENCE: 4
gtggaagctt acacctataa tcccaacact c                              31

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:Synthetic

<400> SEQUENCE: 5
ctgcctggta ccctattgcg atagcaccat ggc                            33

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence:Synthetic

<400> SEQUENCE: 6
aaataattag aaagatatga cttatctcaa atcaa                          35

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence:Synthetic

<400> SEQUENCE: 7
aaataattag aaaggatatg acttatctca aatcaa                         36

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence:Synthetic

<400> SEQUENCE: 8
ttcattgtta atcaagagga tgttataaag catgagtcac accctcagct t         51

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 9
gttatgccac ttagatgagg                                           20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 10
ttcctcccct tatggattcc                                           20
```